United States Patent [19]

Bahl

[11] 4,071,817
[45] Jan. 31, 1978

[54] HIGH TEMPERATURE ELECTROCHEMICAL CELL TESTER

[75] Inventor: George R. Bahl, Springfield, Pa.

[73] Assignee: Suntech, Inc., St. Davids, Pa.

[21] Appl. No.: 664,733

[22] Filed: Mar. 8, 1976

[51] Int. Cl.$^2$ ............................................. G01N 27/42
[52] U.S. Cl. ................................. 324/30 R; 324/30 B; 204/1 T
[58] Field of Search .................. 324/61 R, 61 P, 30 R, 324/30 B; 204/1 S, 195 S, 236, 239, 267

[56] References Cited

U.S. PATENT DOCUMENTS

| | | | |
|---|---|---|---|
| 2,595,814 | 5/1952 | Rich et al. | 324/30 R |
| 3,060,374 | 10/1962 | Strain | 324/30 R |
| 3,159,573 | 12/1964 | Ritchie | 324/30 B |
| 3,265,962 | 8/1966 | Otto | 324/30 B |
| 3,287,638 | 11/1966 | Bolie | 324/30 B |
| 3,400,054 | 9/1968 | Ruka et al. | 204/1 S |
| 3,488,584 | 1/1970 | Ziniuk | 324/30 B |
| 3,864,626 | 2/1975 | MacLean | 324/30 B |

Primary Examiner—M. Tokar
Attorney, Agent, or Firm—J. Edward Hess; Donald R. Johnson; Anthony Potts, Jr.

[57] ABSTRACT

A method for testing the electrolyte of a high temperature electrochemical cell and a system for carrying out this testing method so that the condition of the electrolyte can be monitored during its use. The method includes impressing an alternating current across the electrodes of the electrolyte of the high temperature electrochemical cell to determine the resistance of the electrolyte and the electrodes connected to the electrolyte.

12 Claims, 1 Drawing Figure

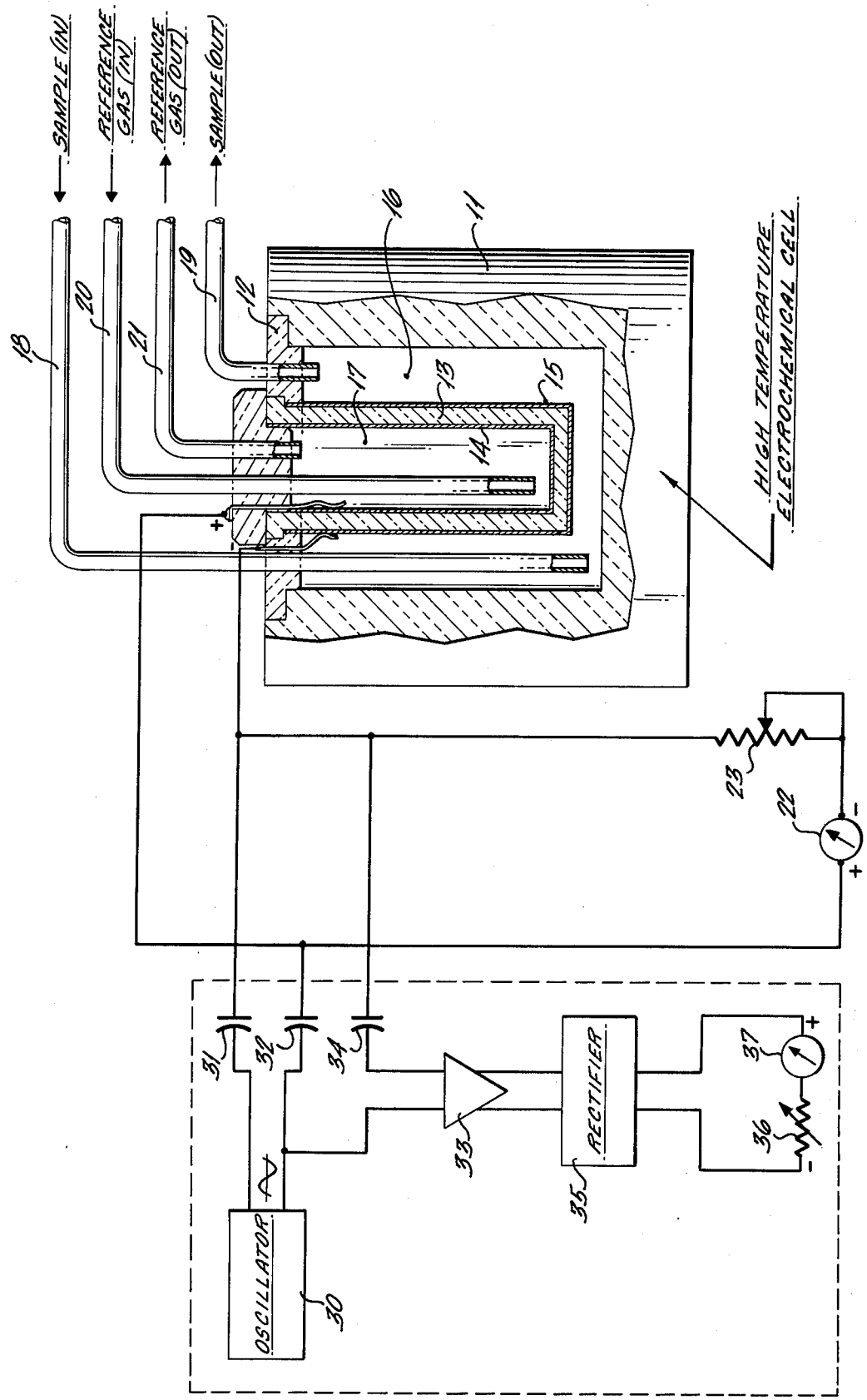

HIGH TEMPERATURE ELECTROCHEMICAL CELL TESTER

BACKGROUND OF THE INVENTION

This invention is related to high temperature electrochemical cells and more specifically to systems for testing the electrolyte of the electrochemical cell while it is in use.

The high temperature electrochemical cell which uses a solid electrolyte is disclosed in U.S. Pat. No. 3,400,054, issued to R. J. Ruka el al. This cell has many uses, many of which are explained in this patent. One popular use for this cell is to monitor the oxygen level of flue gas as an indication of the combustion efficiency of a boiler, incinerator, or other burner device.

As stated in the Ruka patent, the solid electrolyte can be made of a solution of oxides such as zirconium oxide and scandium oxide. Electrodes are attached to either side of the electrolyte. The cell is designed so that the electrolyte forms two isolated chambers, with an electrode on each side of the electrolyte. For purposes of monitoring the oxygen content in the flue gas, a reference gas containing a known concentration of oxygen, or air from the atmosphere, is placed in one chamber and samples from the flue gas are circulated through the other chamber. The electrolyte is then heated and a potential difference is produced between each electrode of the electrolyte. The value of the potential difference is indicative of the ratio of oxygen content in the two chambers. To obtain a reading indicating the amount of oxygen in the flue gas, the potential difference produced can be placed across a resistor in series with an ammeter in a measuring circuit to determine the current produced.

Under normal operating conditions at temperatures from 800° to 1200° C, the electrolyte will have a low resistance between 25 to 100 ohms. However, once the electrolyte or its electrodes start to deteriorate, the resistance in the cell rises and can greatly affect the value read by the ammeter. As a result, when the electrolyte or electrodes start to deteriorate, the process operator detects only a gain in oxygen level and does not realize that the electrolyte deterioration is actually changing the value. Obviously, this can lead to improper control of the burning process.

Therefore, it is desirable to have some system for monitoring the quality of the electrolyte and its electrodes continuously while the electrochemical cell is being used so that when an operator determines the oxygen content of the flue gas he also knows that this is the actual oxygen content and that the reading is not being affected by a defective electrolyte or electrode.

SUMMARY OF THE INVENTION

In accordance with a preferred embodiment, a testing system is disclosed which connects to the electrodes of the electrolyte in a high temperature electrochemical cell and can provide continuous monitoring of the quality of the electrolyte and electrodes while using the electrochemical cell. The testing system is capacity coupled to the electrodes of the electrolyte and includes a low frequency oscillator for impressing an alternating current across the electrodes, an alternating current amplifier receiving the output from the signals being placed across the electrodes, a rectifier for converting the alternating current output of the amplifier to a DC signal, and a circuit for measuring the current output of the rectifier.

This system has the advantage that it permits continuous monitoring of the quality of the electrolyte while the electrochemical cell is being used to monitor the oxygen content of the flue gas. In addition, since the condition of the cell can be continuously monitored, the reading of the cell can be continuously calibrated. The need for periodically removing the electrochemical cell and disassembling it to test the electrodes and electrolyte is also eliminated. Another advantage for testing the electrochemical cell while it is being used is that the electrolyte and electrodes are tested at their operating temperature so that the operational resistance is measured.

The invention and its advantages may be more fully understood by referring to the following figure and description of the preferred embodiment.

DESCRIPTION OF THE FIGURE AND PREFERRED EMBODIMENT

The FIGURE illustrates in schematic form a typical high temperature electrochemical cell design and a circuit diagram of the testing system and its preferred manner for connection to the electrodes of the electrolyte.

The high temperature electrochemical cell has an insulated enclosure 11 with an insulated enclosure cover 12 in which is secured a cylindrical electrolyte 13. Inner electrode 14 and outer electrode 15 are applied to the inner and outer sides of electrolyte 13 in the form of a thin coating. For purposes of explanation, inner electrode 14 will be designated as the anode and outer electrode 15 will be designated as the cathode. The space between the inside of enclosure 11 and the outside of electrolyte 13 can be designated as sample chamber 16. The space inside electrolyte 13 can be designated as reference chamber 17.

Sample chamber 16 has an inlet tube 18 which extends down near the bottom of the chamber and an outlet tube 19 at its top. Sample chamber 17 also has an inlet tube 20 which extends near the bottom of the chamber and an outlet tube 21 at the top. The cathode and the anode are connected across a load such as ammeter 22 and a variable resistor 23. When the electrochemical cell is heated (by means not shown) the amount of current flowing through ammeter 22 due to the potential difference created by electrolyte 13 and placed across resistor 23, is related to the oxygen content of the flue gas being sampled. As stated above, a typical manner of operation would use a reference gas with a known oxygen content in the reference chamber 17 and the flue gas will be circulated through sample chamber 16 in which a potential difference will be created across electrolyte 13 and electrodes 14 and 15 as a result of the difference in oxygen content in the two chambers 16, 17.

The electrolyte and electrode testing system includes a low frequency oscillator 30 which is connected to electrodes 14 and 15 through capacitors 31 and 32 so as to isolate this circuit from the DC component of the electrochemical cell meter circuit and not affect the reading. Oscillator 30 impresses an AC current across electrodes 14, the output of which is received by AC amplifier 33. Capacitors 32 and 34 serve to isolate amplifier 33 from the electrochemical cell meter circuit. The amplified AC output signal is then converted into DC through rectifier 35, the DC output signal then being connected to a variable resistor 36 and ammeter 37. The value of the current passing through resistor 36 is indicative of the resistance value of electrolyte 13 and electrodes 14 and 15. Since the current values are usually quite low, ammeter 37 is preferably a microammeter.

The magnitude of the current is related to the resultant resistance of the electrolyte and electrodes in combination with the components in the measuring circuit, and can be established experimentally or by analytical means. Since the resistance of the electrolyte and electrodes is usually quite low with respect to the resistance of the measuring circuit, the resultant resistance is essentially the same as that of the electrolyte and electrodes.

The dial of ammeter 37 can be calibrated so that it displays the cell resistance in units indicating percentage of failure so that the oxygen level rating obtained from ammeter 22 can be adjusted according to the percentage of failure of electrolyte 13 and electrodes 14 and 15 to provide continuous calibration of the electrochemical cell reading.

While a particular embodiment of this invention has been shown and described, it is obvious that changes and modifications can be made without departing from the true spirit and scope of the invention. It is the intention of the appended claims to cover all such changes and modifications.

The invention claimed is:

1. In an electrochemical cell system having an electrolyte completely separating two chambers with an electrode located on each side of the electrolyte, and which indicates a relationship between the contents of one chamber and the contents of the other chamber by the potential difference created across the two electrodes when the cell is heated to a predetermined high temperature, and has a direct current measuring system for indicating this potential difference, an improvement for detecting the resistance of the combination of the electrodes and electrolyte without removing the electrodes and electrolyte from the electrochemical cell and without interfering with the continuous operation of the cell, said improvement comprising:
    a. means for impressing an alternating current input signal across the electrodes; and
    b. means, responsive to an output alternating current signal from the electrodes, for determining the magnitude of a parameter of the output alternating current, this magnitude being related to the resistance between the two electrodes, said resistance value indicating the quality of the electrodes and electrolyte.

2. The improvement recited in claim 1, further including means for isolating the direct current component of the potential difference measuring system for the impressing means and the receiving means.

3. The improvement recited in claim 1, wherein the determining means includes means for converting the output altenating current signal to a direct current signal and means for determining the magnitude of a parameter of the direct current signal whereby the magnitude of this parameter is related to the resistance of the electrodes and electrolyte.

4. The improvement recited in claim 3, wherein the means for determining the magnitude of a parameter of the direct current signal includes means for determining the magnitude of the current in the direct current signal.

5. The improvement recited in claim 4, wherein the means for determining the magnitude of the current in the direct current signal includes an ammeter and a variable resistor.

6. In an electrochemical cell system having an electrolyte completely separating two chambers with an electrode located on each side of the electrolyte, and which indicates a relationship between the contents of one chamber and the contents of the other chamber by the potential difference created across the two electrodes when the cell is heated to a predetermined high temperature, and has a direct current measuring system for indicating this potential difference, a method for detecting the resistance of the combination of the electrodes and electrolyte in the high temperature electrochemical cell without removing the electrodes and electrolyte from the electrochemical cell, and without interferring with the continuous operation of the cell, said method comprising the steps of:
    a. impressing an alternating current input signal across the electrodes; and
    b. determining the resistance across the electrodes by measuring the magnitude of a parameter of the alternating output current signal from the electrodes, the magnitude of this parameter being related to the resistance of the electrodes.

7. The method recited in claim 6, wherein the step of determining the resistance across the electrodes includes the steps of:
    a. converting the alternating output current signal to a direct current signal; and
    b. determining the magnitude of a parameter of the direct current signal, the magnitude of this parameter being related to the resistance of the electrodes.

8. The method recited in claim 6, wherein the step of determining the magnitude of a parameter of the direct current signal comprises the step of determining the magnitude of the current in the direct current signal, the magnitude of the current being related to the resistance of the electrodes.

9. An electrochemical cell system having a testing system for determining the quality of the electrolyte and electrodes of the electrochemical cell without removal from the cell and without interferring with the continuous operation of the cell, said electrochemical cell system comprising:
    a. housing means for defining an enclosure;
    b. spacing means located in the housing means to form two separate chambers, a reference chamber and a sample chamber, wherein said spacing means comprises an electrolyte with an electrode on each side of the electrolyte, with one electrode in each chamber;
    c. first fluid communication means connecting the reference chamber so that a first fluid can be circulated through the reference chamber, said first fluid having a known amount of oxygen contained therein;
    d. second fluid communication means connecting the sample chamber so that a second fluid can be circulated through the sample chamber, said second fluid having an unknown amount of oxygen contained therein;
    e. means for measuring the direct current potential difference across the electrodes when the electrochemical cell is at a predetermined temperature, said potential difference being related to the relation of the difference in the amounts of oxygen in the chambers;

f. means for impressing an alternating current input signal across the electrodes; and g. means responsive to an output alternating current signal from the electrodes, for determining the magnitude of a parameter of the output alternating current, this magnitude being related to the resistance between two electrodes, said resistance valve indicating the quality of the electrodes and electrolyte.

10. The electrochemical cell system recited in claim 9, further including means for isolating the direct current component of the measuring means from the impressing means and the receiving means.

11. The electrochemical system recited in claim 9, wherein the determining means includes means for converting the output alternating current signal to a direct current signal and means for determining the magnitude of a parameter of the direct current signal whereby the magnitude of this parameter is related to the resistance of the electrodes and electrolytes.

12. The electrochemical cell system recited in claim 11, wherein the means for determining the magnitude of a parameter of the direct current signal includes means for determining the magnitude of the current in the direct current signal.

* * * * *